(12) United States Patent
Demarest et al.

(10) Patent No.: US 11,717,678 B2
(45) Date of Patent: *Aug. 8, 2023

(54) ORAL CARE DEVICE

(71) Applicant: Colgate-Palmolive Company, New York, NY (US)

(72) Inventors: Scott Demarest, Loudon, TN (US); Mark Dobrovolny, Scarborough, ME (US)

(73) Assignee: Colgate-Palmolive Company, New York, NY (US)

( * ) Notice: Subject to any disclaimer, the term of this patent is extended or adjusted under 35 U.S.C. 154(b) by 236 days.

This patent is subject to a terminal disclaimer.

(21) Appl. No.: 16/949,888

(22) Filed: Nov. 19, 2020

(65) Prior Publication Data

US 2021/0346690 A1 Nov. 11, 2021

Related U.S. Application Data

(60) Division of application No. 15/954,109, filed on Apr. 16, 2018, now Pat. No. 10,874,855, which is a
(Continued)

(51) Int. Cl.
*A61N 1/30* (2006.01)
*A61B 5/145* (2006.01)
(Continued)

(52) U.S. Cl.
CPC .......... *A61N 1/306* (2013.01); *A61B 5/14507* (2013.01); *A61B 5/14539* (2013.01);
(Continued)

(58) Field of Classification Search
CPC .. A61C 5/90; A61C 5/82; A61N 1/306; A61B 5/14507; A61B 5/14539; A61B 5/4205; A61B 5/4839; A61B 5/682
See application file for complete search history.

(56) References Cited

U.S. PATENT DOCUMENTS 3,481,329 A 12/1969 Warren, Jr.
3,527,218 A 9/1970 Westine
(Continued)

FOREIGN PATENT DOCUMENTS

EP 1525857 4/2005
JP 2008-272322 11/2008
(Continued)

OTHER PUBLICATIONS

International Search Report and Written Opinion of the International Searching Authority in International Application No. PCT/US2017/067474, dated May 23, 2018.

*Primary Examiner* — Nicholas D Lucchesi (57) ABSTRACT

An oral care device for placement in the oral cavity. The oral care device may include a support component, a piezoelectric component, and/or a therapeutic element. The support component is configured for placement between one or more maxillary teeth and one or more mandibular teeth. The piezoelectric element is configured to generate an electrical current from relative movement of the maxillary teeth and the mandibular teeth. The therapeutic element is configured to release a therapeutic composition into the oral cavity at least in part in response to receiving the electrical signal. The device may include the piezoelectric component, the therapeutic element, or both.

8 Claims, 5 Drawing Sheets

Related U.S. Application Data continuation of application No. 15/390,818, filed on Dec. 27, 2016, now Pat. No. 9,968,777.

(51) Int. Cl.

| | |
|---|---|
| *A61B 5/00* | (2006.01) |
| *H02N 2/18* | (2006.01) |
| *H02J 7/32* | (2006.01) |
| *A61N 1/32* | (2006.01) |
| *A61N 1/05* | (2006.01) |
| *A61C 19/06* | (2006.01) |
| *H10N 30/30* | (2023.01) |
| *H10N 30/80* | (2023.01) |
| *H10N 30/853* | (2023.01) |
| *H10N 30/857* | (2023.01) |
| *A61B 10/00* | (2006.01) |
| *A61N 1/378* | (2006.01) |
| *A61N 1/04* | (2006.01) |

(52) U.S. Cl.
CPC .......... *A61B 5/4205* (2013.01); *A61B 5/4839* (2013.01); *A61B 5/682* (2013.01); *A61C 19/063* (2013.01); *A61N 1/0548* (2013.01); *A61N 1/325* (2013.01); *H02J 7/32* (2013.01); *H02N 2/18* (2013.01); *H10N 30/30* (2023.02); *H10N 30/802* (2023.02); *H10N 30/853* (2023.02); *H10N 30/857* (2023.02); *A61B 2010/0083* (2013.01); *A61B 2562/029* (2013.01); *A61N 1/0428* (2013.01); *A61N 1/3785* (2013.01)

(56) References Cited

U.S. PATENT DOCUMENTS

| | | | |
|---|---|---|---|
| 3,566,869 | A | 3/1971 | Crowson |
| 3,760,799 | A | 9/1973 | Crowson |
| 4,149,533 | A | 4/1979 | Ishikawa et al. |
| 4,560,351 | A | 12/1985 | Osborne |
| 5,104,315 | A | 4/1992 | McKinley |
| 6,089,864 | A | 7/2000 | Buckner et al. |
| 6,893,259 | B1 | 5/2005 | Reizenson |
| 7,044,737 | B2 | 5/2006 | Fu |
| 7,947,508 | B2 | 5/2011 | Tricca et al. |
| 8,091,554 | B2 | 1/2012 | Jiang |
| 8,104,324 | B2 | 1/2012 | Hennig et al. |
| 8,311,632 | B2 | 11/2012 | Pless et al. |
| 8,505,540 | B2 | 8/2013 | Vaska et al. |
| 8,660,669 | B2 | 2/2014 | Nemeh et al. |
| 8,702,682 | B2 | 4/2014 | Atanasoska et al. |
| 8,739,599 | B2 | 6/2014 | Hennig et al. |
| 9,084,859 | B2 | 7/2015 | Connor |
| 9,168,370 | B2 | 10/2015 | Nemeh et al. |
| 9,314,321 | B2 | 4/2016 | Nemeh et al. |
| 9,636,195 | B2 | 5/2017 | Wolpo |
| 9,839,500 | B2 | 12/2017 | Flyash |
| 2006/0115785 | A1 | 6/2006 | Li et al. |
| 2008/0199830 | A1 | 8/2008 | Fontenot et al. |
| 2008/0255498 | A1 | 10/2008 | Houle |
| 2010/0317978 | A1 | 12/2010 | Maile et al. |
| 2013/0042876 | A1* | 2/2013 | Hermanson ............ A61F 5/566 128/848 |
| 2014/0072932 | A1 | 3/2014 | Brawn et al. |
| 2014/0134561 | A1 | 5/2014 | Smith et al. |
| 2014/0261425 | A1 | 9/2014 | Connor |
| 2015/0238691 | A1 | 8/2015 | Boyden et al. |
| 2015/0305671 | A1 | 10/2015 | Yoon et al. |
| 2016/0067081 | A1 | 3/2016 | Sorresso |
| 2016/0089535 | A1 | 3/2016 | Mohammadi et al. |
| 2016/0278899 | A1* | 9/2016 | Heller ................. A61C 19/063 |
| 2017/0216148 | A1 | 8/2017 | Altounian |
| 2018/0000573 | A1 | 1/2018 | Miller |

FOREIGN PATENT DOCUMENTS

| | | |
|---|---|---|
| JP | 2011-083550 | 4/2011 |
| WO | 2007/140784 | 12/2007 |
| WO | 2016/051400 | 4/2016 |
| WO | 2016/137617 | 9/2016 |

* cited by examiner

ORAL CARE DEVICE

CROSS-REFERENCE TO RELATED APPLICATIONS

The present application is a divisional of U.S. patent application Ser. No. 15/954,109, filed Apr. 16, 2018, which is a continuation of U.S. patent application Ser. No. 15/390,818, filed Dec. 27, 2016, now U.S. Pat. No. 9,968,777, the entireties of which are incorporated herein by reference.

BACKGROUND

Various products and processes have been developed to improve and maintain oral health. For example, formulations such as mouthwashes, creams, pastes, salves, and the like, are known for reducing bacteria in the mouth and/or for treating other oral conditions. Conventionally, the formulations are applied to the teeth, gums and/or other areas of the oral cavity by rinsing, brushing, or otherwise. However, there is a need in the art for improved implements and methods for treating the oral cavity.

Accordingly, there is a need in the art for effective oral care devices. This disclosure is directed at overcoming one or more problems set forth above and/or other problems of the prior art.

BRIEF SUMMARY

This application describes improved oral care devices and methods for treating the oral cavity. In some embodiments, an oral care device herein may be embodied as a device for placement in the oral cavity. The device may include a support component, a piezoelectric component, and/or a therapeutic element. The support component is configured for selective retention in the oral cavity and may include a mouthpiece. The piezoelectric element is configured to generate an electrical current from relative movement of anatomy in the oral cavity. For example, the piezoelectric element may be positioned between the maxillary and the mandibular teeth. The therapeutic element is electrically connected to the piezoelectric component and is configured to release a therapeutic agent into the oral cavity, at least in part in response to receiving the electrical signal.

In other implementations, an oral device as described in the preceding paragraph(s) may further include a microcontroller for selectively applying power to the therapeutic element.

In other implementations, an oral device as described in the preceding paragraph(s) may further include a power source for at least one of storing the electrical current generated by the piezoelectric component or providing auxiliary power.

In other implementations, in an oral device as described in the preceding paragraph(s), the piezoelectric component may be disposed on the support component to be positioned between at least one maxillary tooth and the at least one mandibular tooth.

In other implementations, in an oral device as described in the preceding paragraph(s), the piezoelectric element may include an electro-active polymer.

In other implementations, in an oral device as described in the preceding paragraph(s), the active polymer may be coated on an outer surface of the support component.

In other implementations, in an oral device as described in the preceding paragraph(s), the piezoelectric element may include a ceramic crystal.

In other implementations, in an oral device as described in the preceding paragraph(s), the ceramic crystal may be encapsulated in a portion of the support component.

In other implementations, in an oral device as described in the preceding paragraph(s), the therapeutic element may include an iontophoresis element.

In other implementations, in an oral device as described in the preceding paragraph(s), the iontophoresis element may disposed on the support structure such that the iontophoresis element contacts soft tissue in the oral cavity when the support structure is placed between the at least one maxillary tooth and the at least one mandibular tooth.

In other implementations, in an oral device as described in the preceding paragraph(s), the therapeutic element may include an electromechanical dispenser comprising a reservoir holding an active substance and a mechanism for releasing the active substance from the reservoir into the oral cavity.

In other implementations, in an oral device as described in the preceding paragraph(s), the mechanism for releasing the active substance may include a moveable covering or a microfluidic valve.

In other implementations, an oral device as described in the preceding paragraph(s) may further include a sensor for sensing a condition in the oral cavity, the therapeutic composition being released into the oral cavity at least in part in response to sensing the condition and the sensor sensing at least one of humidity, pH, swallowing frequency, targeted bacteria, saliva markers, or gas phase components.

In other implementations, an oral device as described in the preceding paragraph(s) may further include electronics configured to at least one of receive data from the sensor or control the therapeutic element to release the therapeutic composition.

In other implementations, in an oral device as described in the preceding paragraph(s), the electronics may include a controller for controlling application of an electrical current to the therapeutic element based on the data from the sensor.

In yet another implementation of this disclosure, an oral device for placement in the oral cavity may include a support component configured for placement between one or more maxillary teeth and one or more mandibular teeth; a therapeutic element disposed on the support component and configured to release a therapeutic composition into the oral cavity at least in part in response to receiving an electrical current; and a battery disposed on the support component for supplying the electrical current.

In other implementations, an oral device as described in the preceding paragraph(s) may further include a piezoelectric component disposed on the support component and configured to generate an electrical current from relative movement of anatomy in the oral cavity.

In other implementations, in an oral device as described in the preceding paragraph(s), the piezoelectric component may include an electro-active polymer or a ceramic crystal.

In other implementations, in an oral device as described in the preceding paragraph(s), the therapeutic element may include an iontophoresis element.

In other implementations, an oral device as described in the preceding paragraph(s) may further include a sensor for sensing a condition in the oral cavity, the therapeutic composition being released into the oral cavity at least in part in response to sensing the condition and the sensor sensing at least one of humidity, pH, swallowing frequency, targeted bacteria, saliva markers, or gas phase components.

In other implementations, methods for providing oral benefits are provided. For instance, methods according to this disclosure may include converting mechanical energy, e.g., from a wearer clenching her jaw or grinding his teeth, to electrical energy, and using the electrical energy to power a therapeutic element disposed in the oral cavity. The therapeutic element may be an iontophoresis patch, for example.

In one aspect, the invention may be an oral care device comprising: a support component configured for retention in an oral cavity; a piezoelectric component disposed on the support component and configured to generate an electrical current from mechanical forces created by relative movement of anatomy in the oral cavity; and a storage system operably coupled to the piezoelectric component, the storage system configured to store the electrical current generated by the piezoelectric component.

In another aspect, the invention may be an oral care device comprising: a support component configured for placement in an oral cavity between one or more maxillary teeth and one or more mandibular teeth, the support component comprising a base portion having an inner surface and a web portion extending between portions of the inner surface; and a therapeutic element disposed on the web portion of the support component and configured to release a therapeutic composition into the oral cavity at least in part in response to receiving an electrical current.

In yet another aspect, the invention may be an oral care device comprising: a support component configured for retention in an oral cavity, the support component comprising a base portion and first and second sidewalls extending from the base portion in a spaced apart manner, the base portion and the first and second sidewalls defining a receptacle for receiving a wearer's teeth, the first sidewall having an outer surface facing away from the receptacle; and a first therapeutic element disposed on the outer surface of the first sidewall and configured to release a first therapeutic composition into the oral cavity at least in part in response to receiving an electrical current.

Further areas of applicability of the present disclosure will become apparent from the detailed description provided hereinafter. It should be understood that the detailed description and specific examples, while indicating embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of the preferred embodiments is merely exemplary in nature and is in no way intended to limit the disclosure, its application, or uses.

As used throughout, ranges are used as shorthand for describing each and every value that is within the range. Any value within the range can be selected as the terminus of the range. In addition, each reference cited herein is hereby incorporated by reference in its entirety. In the event of a conflict in a definition in the present disclosure and that of a cited reference, the present disclosure controls.

This disclosure relates generally to oral care implements, and more particularly to oral care implements capable of being partially or completely placed within the oral cavity to provide a benefit to the wearer. In some implementations, the oral care device may include a support structure sized and shaped for retention in the oral cavity. For example, the support structure may include a mouthpiece configured as a mouthguard, a bite plate, or an occlusal splint.

Oral care devices according to this disclosure may also include a piezoelectric component, e.g., disposed on or otherwise incorporated into the support structure. The piezoelectric component may be positioned such that when a wearer places the mouthpiece in the intended position in the oral cavity, the piezoelectric component is positioned between at least one maxillary tooth and at least one mandibular tooth. In this manner, pressure is applied to the piezoelectric element when the user clenches her jaw, e.g., while sleeping. This applied pressure is converted to electrical energy by the piezoelectric element. In different embodiments, the piezoelectric element may include an active polymer and/or a crystal, such as a ceramic crystal.

Electrical energy generated by the piezoelectric element may be used to power a therapeutic element. In some embodiments, the electrical energy may be harvested, e.g., stored in a storage system, and applied to the therapeutic element from the storage system. Controls may also be provided to control application of electrical current from the storage system to the therapeutic element. Alternatively, the therapeutic element may be electrically connected, e.g., via leads or the like, to the piezoelectric element to directly receive current from the piezoelectric element.

The therapeutic element may include any number of electromechanical devices capable of delivering a therapeutic agent to the oral cavity. By way of non-limiting example, the therapeutic element may include an active iontophoresis element, which may be an iontophoresis patch. The element may be disposed on the mouthpiece in a manner that positions the therapeutic element to deliver the therapeutic agent. For example, when the element is an iontophoresis element, the element may positioned on the mouthpiece to contact soft tissue, e.g., an inside of the cheek, the tongue, the pallet, the gums, or the like when the mouthpiece is worn. In other implementations, the therapeutic element may be positioned to contact one or more teeth, e.g., to apply an anti-cavity agent, such as a fluoride or zinc solution.

In one example implementation, devices according to this disclosure are worn by a user at bedtime. In this manner, when the user grinds or gnashes his teeth while asleep, electrical energy is produced to power the therapeutic element. The therapeutic element may combat dry mouth, for example, which can result in halitosis.

Although certain embodiments and benefits will be described, other implementations, modifications, and/or benefits will be appreciated by those having ordinary skill in the art, with the benefit of this disclosure. For example, the following detailed description may generally refer to embodiments of the inventive implements in the context of a mouthpiece, but the disclosure is not limited to mouthpieces; other oral care implements may also incorporate features of this disclosure.

Figure 1:
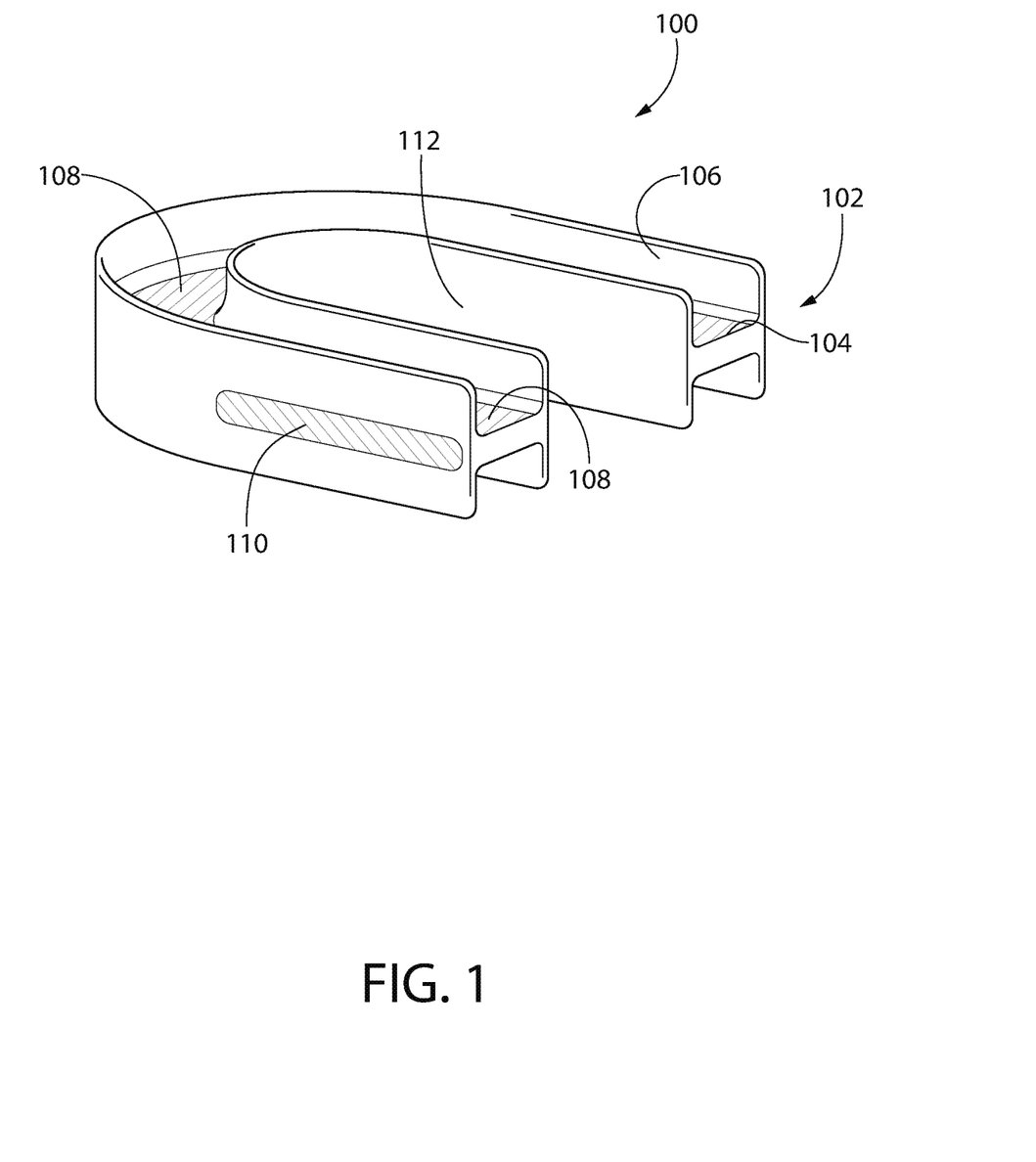
FIG. 1 is a perspective view of an oral care device according to an example implementation of this disclosure.

FIG. 1 illustrates an oral device 100 according to implementations of this disclosure. The oral device 100 comprises a wearable appliance generally configured as a mouthpiece 102. The mouthpiece may be shaped generally as a bite plate, a mouthguard, an occlusal splint or the like. The shape of the illustrated mouthpiece 102 is known in the art, and generally consists of a U-shaped base 104 and a sidewall 106 extending generally from a periphery of the base 104. As will be appreciated, the base 104 is generally configured for positioning to extend along one or more teeth between the maxillary and the mandibular teeth. The sidewall 106 is generally configured to extend along an outer (i.e., facial) surface of at least one tooth. As also illustrated in FIG. 1, a second, inner sidewall 112 is also provided, spaced from the sidewall 106 for contacting an inner surface of at least one tooth. In other embodiments, only one of the sidewalls 106, 112 may be provided, and still allow for retention of the mouthpiece 102 in the oral cavity As illustrated, the base 104 and the sidewall 106 generally define a tray or receptacle to receive a wearer's teeth. In some implementations, the dimensions of the mouthpiece may be customized for a user, or the mouthpiece may be provided in one more predetermined or generic sizes. In the illustrated mouthpiece 102 the sidewalls 106, 112 extend both above and below the base, such that the mouthpiece 102 is generally configured for placement on both the maxillary teeth and the mandibular teeth, although in other embodiments the sidewalls 106, 112 may extend in only one direction from the base 104, rendering the mouthpiece suitable for placement only on the maxillary or the mandibular teeth. By way of non-limiting example, and although not illustrated, in some embodiments only the outer sidewall 106 may be provided, and the sidewall depends only upwardly from the base. In such an embodiment, the base and sidewall may form an L-shaped cross-section, instead of the H-shaped cross-section illustrated. Other modifications will be appreciated by those having ordinary skill in the art.

In other embodiments, the mouthpiece may take other forms and shapes. Regardless of construction, the mouthpiece may serve two purposes. First, the mouthpiece 102 may retain the oral device 100 in the oral cavity. Second, the mouthpiece may serve as a support for a number of additional components used in the device 100. For instance, in the embodiment illustrated in FIG. 1, the mouthpiece 102 supports a piezoelectric component 108 and a therapeutic element 110. The piezoelectric component 108 and the therapeutic element 110 will be described in more detail below.

In the embodiment illustrated in FIG. 1, the piezoelectric component 108 is disposed on the mouthpiece 102, e.g., on the base 104 of the mouthpiece 102, such that the piezoelectric component 108 is positioned between the maxillary and the mandibular teeth when the mouthpiece is positioned in a wearer's mouth. In this manner, when the wearer applies a pressure to the piezoelectric element, e.g., by moving his/her jaw, biting down on the piezoelectric element, grinding her teeth, or the like, an electrical current is generated at the piezoelectric component 108. In other embodiments, the piezoelectric element 108 may be placed between soft tissue, e.g., the tongue and the soft pallet, or between soft tissue and teeth. Specifically, the piezoelectric element 108 may be configured for placement between any intraoral surfaces that will move relative to each other and can apply sufficient force to the piezoelectric element.

The piezoelectric component 108 may be embodied as any number of devices that convert mechanical energy, e.g., resulting from a pressure between the maxillary and the mandibular teeth, to electrical energy. For example, the piezoelectric component may comprise an active polymer, and the active polymer may be disposed on the base 104 of the mouthpiece 102. As illustrated schematically in FIG. 1, the active polymer may be disposed on a top surface of the base 104, i.e., proximate the sidewall 106, such that the piezoelectric component contacts the maxillary teeth when the mouthpiece is positioned in the oral cavity. In alternative embodiments, an electro-active polymer may additionally or alternatively be placed on an opposite surface of the base 104, i.e., for contacting one or more mandibular teeth. The electro-active polymer may be encapsulated within the device to prevent direct contact by the user. Active polymers useful as the piezoelectric component may include known ferroelectric polymers such as polyvinylidene fluoride (PVDF), or the like. In some examples, an active polymer piezoelectric component 108 may be provided as a film adhered or otherwise affixed to the mouthpiece 102. Moreover, a protective covering or film may be disposed over the active polymer, i.e., such that the active polymer is disposed between the mouthpiece 102 and the protective covering. In this arrangement, saliva and other elements in the oral cavity do not contact the piezoelectric component 108 directly.

In other embodiments, the piezoelectric component 108 may be a crystal material, such as a ceramic crystal. For example, the piezoelectric component 108 may include either a naturally-occurring crystal, e.g., quartz, or a synthetic crystal, e.g., lead zirconate titanate (PZT). In examples of this disclosure, a synthetic compound may be preferable, e.g., because it may be easier to control safety-related factors of the piezo material, and the device is intended for use in the mouth. Other crystalline and/or ceramic materials may also be used, as will be appreciated by those having ordinary skill in the art, with the benefit of this disclosure. Depending on the piezoelectric material used, it may be undesirable to have the piezoelectric component exposed to the oral cavity, e.g., because the acidity and/or moisture in the cavity may deteriorate or otherwise harm the component. Accordingly, in some embodiments, the piezoelectric element may be encapsulated, e.g., by a protective and orally-suitable polymer. In some examples, the piezoelectric component may be encapsulated by the material forming the mouthpiece. For instance, the mouthpiece may be molded, e.g., by injection molding techniques, around the piezoelectric component 108 to encapsulate the component in the base 104 of the mouthpiece 102.

Although only a single piezoelectric component is illustrated in FIG. 1 and described above, multiple piezoelectric elements may be provided. For example, one piezoelectric element may be provided for placement between molars on the left side of the mouth and a second piezoelectric element may be provided for placement between molars on the right side of the mouth. In other embodiments, more piezoelectric components may be provided, for example, corresponding to different teeth or groups of teeth. The number, size and composition of the piezoelectric elements may also vary depending upon the amount of electrical energy desired to be generated. For example, the piezo-electric polymer coefficient (D33) may range between about −15 and about −40 pC/N (Picocoulombs/Newton).

In embodiments of this disclosure, energy generated by the piezoelectric elements may be harvested or stored in a storage system, e.g., employing a battery or capacitor-based energy storage system. From the storage system, harvested power may be used to power electronic elements on the device 100, including the therapeutic element 110. Electronic controls, e.g., a microcontroller, may also be provided, to selectively apply current generated at the piezoelectric component 108 to the therapeutic element 110. In other embodiments, the storage system may not be used. Instead, the piezoelectric component 108 may be electrically connected to the therapeutic element 110 via a current control circuit, e.g., to promote release of the therapeutic agent from the therapeutic element 110. For example, electrical leads (not shown) may electrically connect the piezoelectric component 108 to the therapeutic element 110, such that when a sufficient current is created at the piezoelectric component, the therapeutic element is activated.

The therapeutic element 110 generally includes an electromechanical device that performs a therapeutic function, e.g., by releasing a therapeutic agent, in response to an electrical input. In a presently preferred embodiment, the therapeutic element 110 may be an iontophoresis element, for example, configured as a patch, that releases a therapeutic composition when current is applied to the element. In the illustrated embodiment, the element 110 is disposed on an external surface of the sidewall 106, such that the element 110 contacts an inner surface of the wearer's cheek. In this manner, the element 110 is positioned to drive a charged therapeutic substance, e.g., a mediation or bioactive, through the soft tissue, using repulsive electromotive forces.

Figure 2:
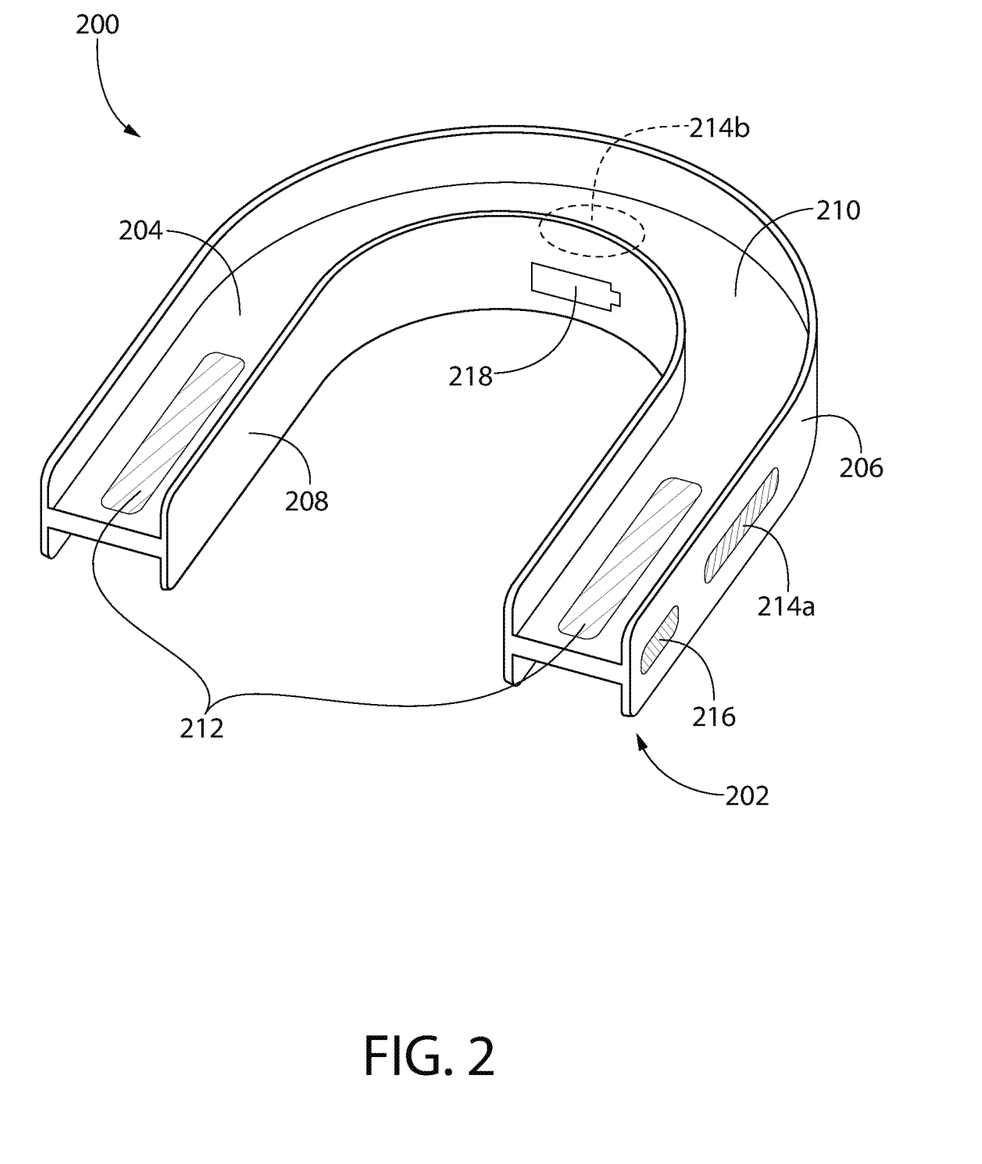
FIG. 2 is a perspective view of an alternative oral care implement, according to an example implementation of this disclosure.

In other embodiments, the therapeutic element, e.g., the iontophoresis element, which will generate about 0.5-1 mA, and may be disposed at a different location on the mouthpiece 102. For example, the sidewall 106 may extend sufficiently from the base 104 that an iontophoresis element disposed on an internal surface of the sidewall 106 proximate a distal end of the sidewall 106 contacts the wearer's gum. In other embodiments, the iontophoresis patch could be configured on the mouthpiece 102 for close contact with other soft tissue. An example of an alternative placement is illustrated in FIG. 2, for example, and will be described in more detail below. Of course, multiple therapeutic elements could also be incorporated into the oral device 100. Other embodiments also are contemplated and will be discussed along with additional implementations described below and/or will be apparent to those having ordinary skill in the art with the benefit of this disclosure.

The therapeutic element 110 is not limited to the iontophoresis patch shown in FIG. 1. For example, in other embodiments, the therapeutic element could include one or more reservoirs containing the therapeutic agent, with the agent being dispensed using a microfluidic pump or valve system. The pump/valve system may be configured, e.g., programmed or controlled, to control release of the agent. More specifically, an amount of the agent, the timing of agent dispensing, and/or dispensing patterns may be controlled by the pump/valve system. In other embodiments, an actuator may be selectively actuated to permit flow of the therapeutic agent from a reservoir. For example, the actuator may break the reservoir, e.g., by mechanical piercing or squeezing, pneumatic pressure, or electrical surface disruption. Multiple, discrete reservoirs may be provided in such examples to allow for disparate dosing. Some such alternate arrangements are described in more detail, below.

According to embodiments of this disclosure, the therapeutic element 110 preferably releases a therapeutic agent into the oral cavity or a surface in the oral cavity, e.g., soft tissue such as the pallet, tongue, gums, and/or inner cheeks or on the teeth. The therapeutic agent may be chosen for its active ingredients useful to treat one or more of dry mouth, malodorous breath, enamel erosion, bacteria growth, or the like. Therapeutic agents may also protect the teeth against cavity formation (in which case the therapeutic element may dispense a therapeutic agent onto the teeth instead of the soft tissue) and/or protect against periodontal disease. In still other applications, the therapeutic agent may be useful to provide therapy against non-oral maladies. For instance, the devices according to this disclosure could provide any of a number of agents, including pain relievers, nutritional supplements, or the like. Moreover, one or more therapeutic agents may be contained in a single device 100. A benefit of multiple therapeutic agents dispensed while sleeping can result in a positive user experience, e.g., waking with fresh breath and clean feeling hard and soft tissue with therapeutic benefit to the hard or soft tissue.

In embodiments of the disclosure all or a portion of the therapeutic element may be selectively replaced, e.g., to refill or replenish the therapeutic agent. By way of non-limiting example, an iontophoresis patch may be replaced with a new patch after a certain number of uses or after an elapsed time, for example. Upon its securing, a replacement patch may also be electrically connected to the piezoelectric element. In still other examples, when the therapeutic agent is included as a reservoir, the reservoir may be selectively replaced with refills and/or with reservoirs containing additional or different agents. In one example, a reservoir containing a therapeutic agent may comprise an insert retained in the mouthpiece, which insert is removed and replaced.

FIG. 2 illustrates another example oral care device 200 according to this disclosure. The device 200 is similar to the device 100 in that it is generally shaped like a conventional mouthguard. More specifically, the device 200 generally includes a support structure shaped as a mouthpiece 202 including a base 204 for positioning between the upper and lower teeth and a sidewall 206 extending from the base for positioning along the sides of the teeth. Reference numeral 206 specifically designates an outer sidewall, i.e., for positioning next to an outer (facial) surface of the teeth, and an inner sidewall 208, i.e., for positioning next to an inner (lingual) surface of the teeth, is also illustrated. In other embodiments, only one of the inner sidewall or the outer sidewall may be needed. In still other embodiments, the sidewalls may not be necessary, as other configurations, designs, and mechanisms may be suitable for retaining the mouthpiece 202 in the oral cavity of the user. As also illustrated in FIG. 2, the mouthpiece 202 also includes a web or plate 210 extending between the sidewalls proximate the front of the device 200. The plate 210 is configured for placement proximate the wearer's soft pallet, as in some conventional orthodontic retainers.

The device 200 also includes two piezoelectric elements 212. The piezoelectric elements 212 may be polymer-type piezoelectric elements that are disposed proximate distal ends of the base 204, e.g., for placement between the molars when the device 200 is worn. The piezoelectric elements 210 may be encapsulated by a polymer such that they are not directly exposed to the oral cavity. For example, the piezoelectric elements 210 may be encapsulated in the base 204 of the mouthpiece 202.

Two therapeutic elements 214a, 214b also are illustrated. The therapeutic element 214a is disposed on the sidewall 206 and is adapted to be placed in close proximity to the inner cheek of the wearer. The therapeutic element 214b is placed on the plate 208, for contacting the soft pallet of the wearer. Both of the therapeutic elements 214a, 214b may be iontophoresis patches, or some other type of element, such as those described above.

As also illustrated in FIG. 2, the device 200 may also include a power source 216. The power source 216 may be a battery provided to power one or more of the components of the device. For example, the power may supplement the electrical power generated by the piezoelectric components 212. This power supplementing may be necessary when additional therapeutic elements 214 or other electronic components are provided, or in the event that the piezoelectric element malfunctions. Moreover, the power source 216 may be electrically connected to the piezoelectric element(s) to store electrical energy generated at the piezoelectric element, e.g., by incorporating a capacitor. In still other embodiments, the power source may obviate the need for the piezoelectric elements altogether.

One or more sensors 218 also are included on the device 200. The sensors 218 may be any number of intraoral sensors for sensing one or more conditions of the oral cavity. For example, the sensors 218 may sense one or more of a humidity in the oral cavity, a pH level of the oral cavity, a swallowing frequency, targeted bacteria within the oral cavity, saliva markers, gas phase markers, or the like. Data from the sensors may be collected for subsequent review and diagnosis, for example, in an on-board memory. In still other embodiments, information about the sensed data may be transmitted to an external device, e.g., a smart phone or other computing device. In some preferred examples, administration of the therapeutic agent from either or both of the therapeutic elements 214a, 214b may be based at least in part on the sensed data. For instance, when the sensors indicate that conditions in the mouth, e.g., pH or humidity, are conducive to bacterial growth, one or both of the therapeutic elements 214a, 214b may be controlled to selectively administer an antibacterial agent. An on-board microcontroller (not shown) may be provided to process the sensor data and activate the therapeutic element to dispense the therapeutic agent, or some or all of the functionality may be done by a remote device, such as a smartphone or an external computing device. In still other embodiments, a microcontroller or an external device may be used to control administration of the therapeutic agent. For example, a user may program a dispensing pattern into an application accessible via a computing device prior to going to sleep at night.

As noted above, in embodiment of this disclosure, different therapeutics may be administered to the oral cavity via a therapeutic element, e.g., therapeutic elements 110, 214a, 214b. In the foregoing examples, the therapeutic elements may be configured as iontophoresis patches, although alternative therapeutic elements may be used instead. In alternative embodiments, the therapeutic element may be a low-level electrical pulse applied to some portion of the oral cavity. For example, it may be possible to stimulate saliva production using low-energy electrical pulses, and the therapeutic element may be configured to provide such a benefit in some examples. Moreover, FIGS. 3, 4, 5A and 5B illustrate alternative embodiments in which different therapeutic elements are used to release a therapeutic agent into the oral cavity.

Figure 3:
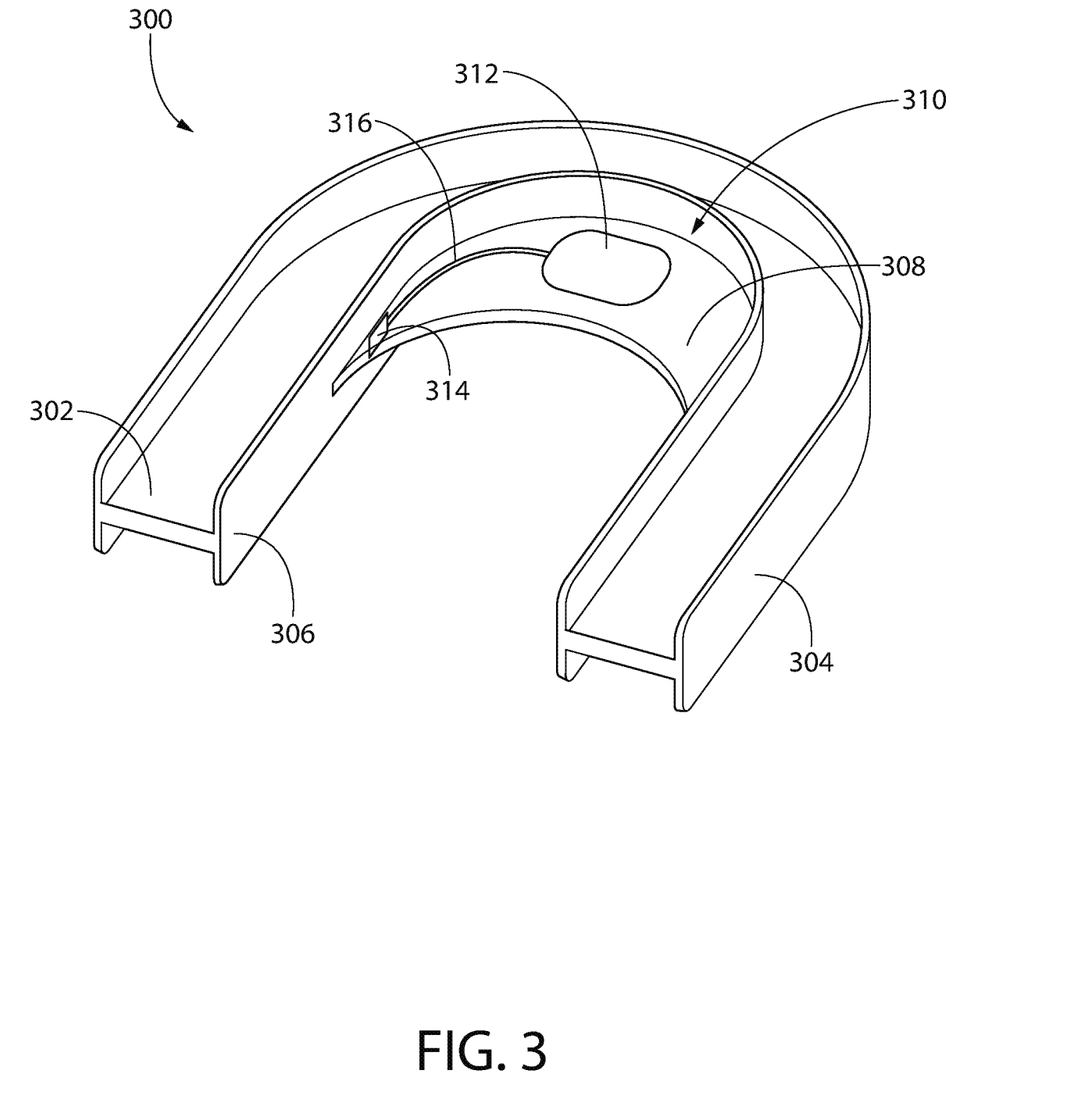
FIG. 3 is a perspective view of an alternative oral care implement, according to another example implementation of this disclosure.

FIG. 3 illustrates another mouthguard-type oral device 300, having a generally U-shaped base 302 with an outer sidewall 304 and an inner sidewall 306 extending therefrom to form a channel for receiving one or both of maxillary and mandibular teeth. Also, a web 308 or other support extends between portions of the inner sidewall 306. A therapeutic element 310 is disposed on the web 308. Specifically, the therapeutic element includes a reservoir 312 containing a therapeutic agent, e.g., a liquid, gel or powder. Release of the therapeutic agent may be controlled by a valve 314 in fluid communication with the reservoir 312. In the illustrated embodiment, the valve 314 is spaced from the reservoir 312 by a conduit 316, e.g., a tube, although the valve 314 may be directly connected to the reservoir.

In operation, the reservoir may be pressurized, e.g., by a pump such as a microfluidic pump, an elastic membrane, a piston, or the like, and the valve is selectively opened to dispense the agent from the reservoir. In some embodiments, the valve may be a microvalve controllable by controls, not shown. In some embodiments, the controls may be disposed on or integrated into the device 300. Moreover, sensors may be provided on the device 300, with the valve being configured to dispense the therapeutic agent according in response to a sensed condition, as in embodiments described above. Although the therapeutic element 310 is illustrated as being disposed on the web 308, some or all portions may be otherwise disposed, e.g., on the sidewalls 304, 306 and/or on the base 302. In some instances, the web 308 may not be necessary. As with previous embodiments, components of the therapeutic element 310 may be powered by an on-board power source, which may include a piezoelectric element that converts mechanical energy to electrical power.

Figure 4:
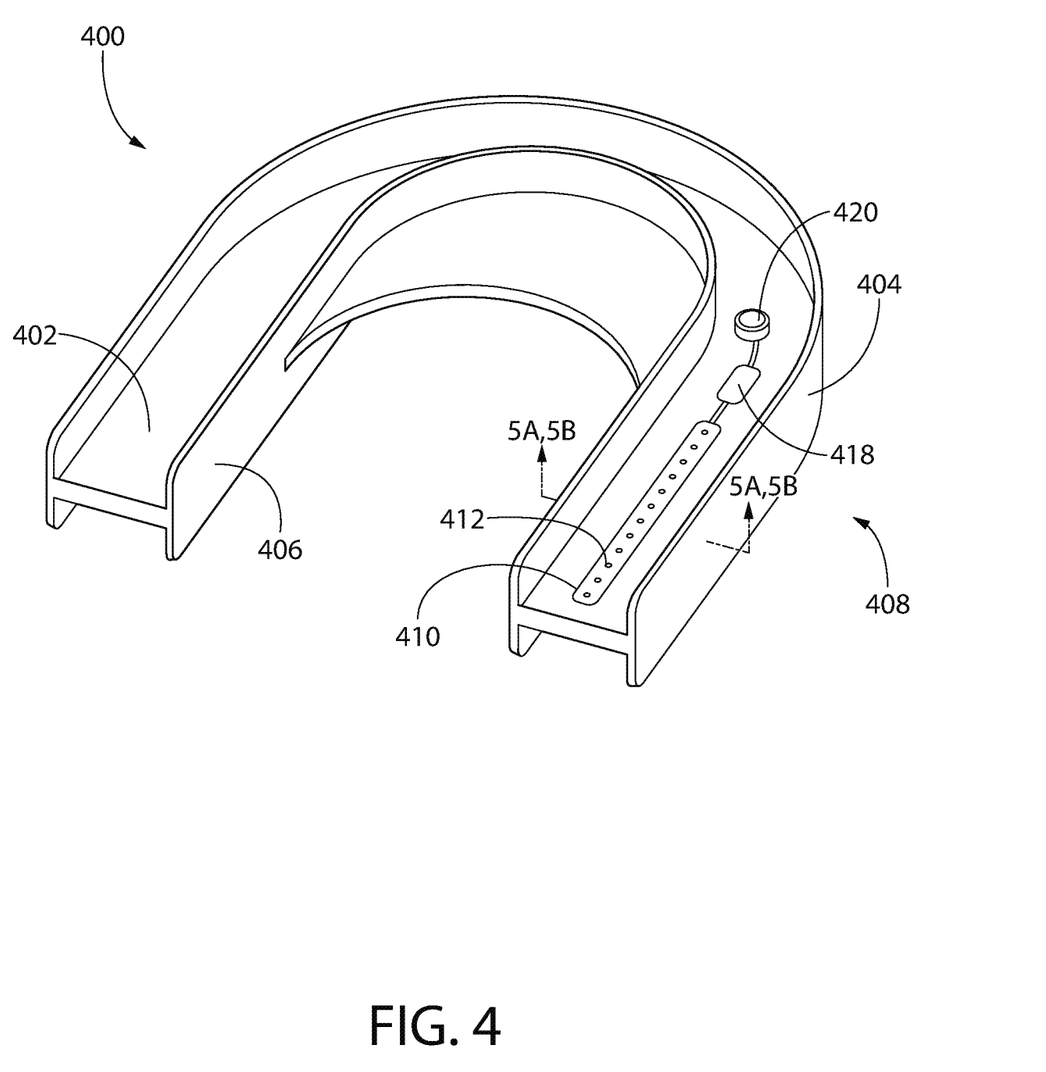
FIG. 4 is a perspective view another oral care implement, according an additional example implementation of this disclosure.

FIG. 4 illustrates another device 400 that has a similar structure to those described above. More specifically, the device 400 includes a U-shaped base 402, an outer sidewall 404 and an inner sidewall 406. The base 402, the outer sidewall 404 and/or the inner sidewall 406 promote retention of the device 400 in the oral cavity. A therapeutic element 408 also is provided in this embodiment. The therapeutic element generally includes a reservoir 410 and one or more holes 412 through the reservoir 410. Each of the holes 412 provides fluid communication between an interior of the reservoir 410 and an exterior of the reservoir 410 (i.e., the oral cavity when the device is placed in the mouth).

Figure 5A:
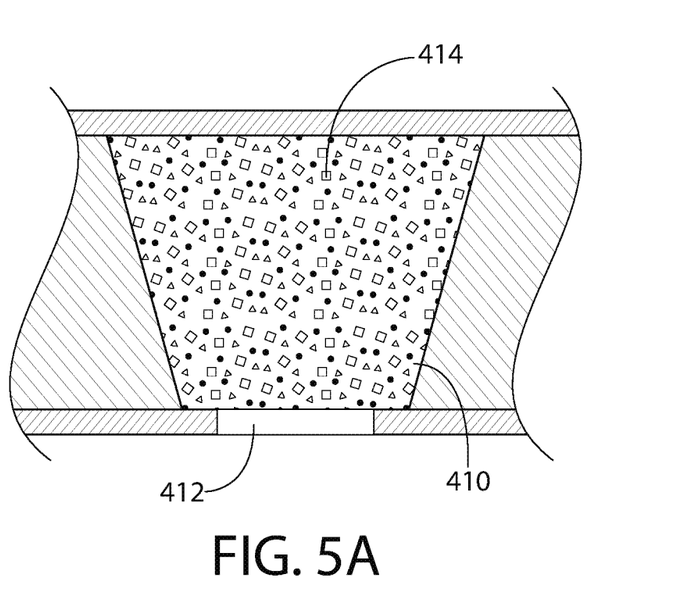
FIGS. 5A and 5B are a cross-sectional view taken along section line 5A, 5B-5A, 5B of FIG. 4.
Figure 5B:
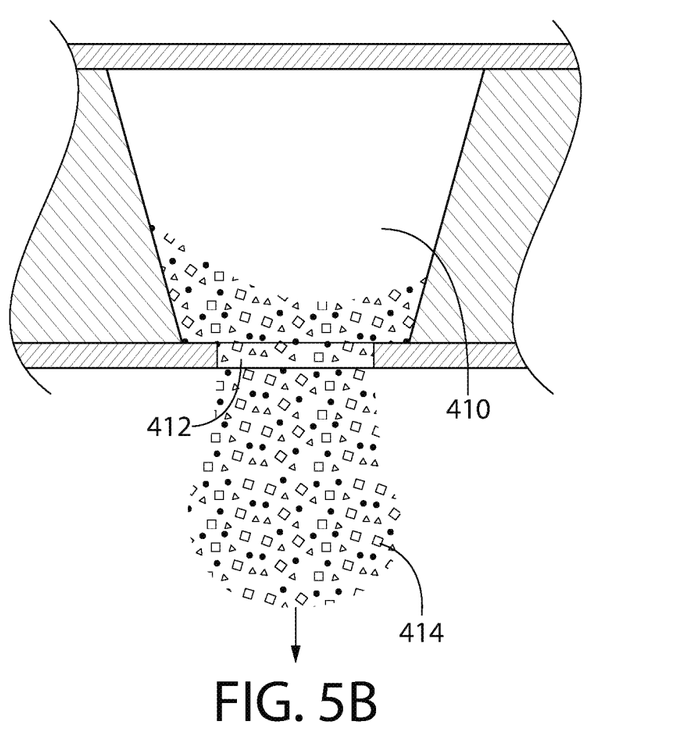

As detailed in FIG. 5A, the reservoir 410 retains a therapeutic agent 414, and each of the holes 412 is closed with a covering 416. As in FIG. 5B, the coverings 416 may be selectively removed from the holes 412, allowing the therapeutic agent 414 to flow out of the reservoir 410 and into the oral cavity, via the opening. The coverings may be actuatable between an open position and a closed position, they may be punctured, e.g., by a needle or other actuator, or they may be rupturable or frangible. In some embodiments, a conductive trace may be provided in the covering and under an applied electrical current, the trace may heat up and melt or otherwise rupture the covering 416. The reservoir 410 may include a plurality of discrete compartments, e.g., such that the compartments have a one-to-one correspondence with the holes 412, and different compartments may contain different therapeutic agents. Alternatively, multiple holes may provide access to a single reservoir, e.g., to promote release of the same agent at multiple locations.

As illustrated in FIG. 4, the therapeutic agent may also include controls 418, e.g., a microcontroller, and a power source 420. As with other embodiments, sensors may also be included on the device 400, as may a piezoelectric element. Although the components of the device 400 are illustrated as being disposed on the base 402, some or all components may be disposed elsewhere on the device 400. For example, it may be desirable to place the reservoir 410 such that the holes open downward (as in FIGS. 5A and 5B) so gravity may assist in evacuating the therapeutic agent 414 through the holes 412. The reservoir may also be larger, i.e., to cover more area and/or to hold more therapeutic agent. Other modifications will also be contemplated by those having skill in the art, with the benefit of this disclosure.

As will be appreciated, according to the foregoing embodiments, an oral device is illustrated and described that can be used to administer a therapeutic agent inside the oral cavity. The therapeutic element is preferably an electromechanical device that is powered by electrical current generated by a piezoelectric element. In one example use case, the device may be worn at night, while the wearer sleeps. Many people clench, grind or otherwise move their jaws and teeth during sleep, and devices according to this disclosure harvest that mechanical energy as electrical energy used to power an on-board therapeutic element. In some embodiments, a separate power source is not required, so batteries do not lose their charge or otherwise need replacing or re-charging. Instead, the device 100, 200 is self-contained and easily used.

The present disclosure describes oral care devices that are effective and relatively simple to use. The devices described herein may provide a therapeutic effect within the oral cavity without the need for external powering or user interaction. Moreover, devices described herein may allow a user to administer therapeutic agents Although example embodiments have been described in language specific to the structural features and/or methodological acts, the claims are not necessarily limited to the specific features or acts described. Rather, the specific features and acts are disclosed as illustrative forms of implementing the example embodiments.

What is claimed is:

1. An oral care device comprising:
   a support component configured for retention in an oral cavity;
   a piezoelectric component disposed on the support component and configured to generate an electrical current from mechanical forces created by relative movement of anatomy in the oral cavity; and
   a storage system operably coupled to the piezoelectric component, the storage system configured to store the electrical current generated by the piezoelectric component.

2. The oral care device of claim 1 wherein the storage system comprises a power source.

3. The oral care device of claim 1 wherein the piezoelectric component is disposed on the support component to be positioned between at least one maxillary tooth and at least one mandibular tooth.

4. The oral care device of claim 1 wherein the piezoelectric component comprises an electro-active polymer that is coated on an outer surface of the support component.

5. The oral care device of claim 1 wherein the piezoelectric component is encapsulated in a portion of the support component.

6. The oral care device of claim 1 further comprising a sensor disposed on the support component, the sensor configured to sense a condition in the oral cavity.

7. The oral care device of claim 6 further comprising a controller operably coupled to the sensor and configured to receive data from the sensor.

8. The oral care device of claim 1 wherein the support component comprises a base portion and at least one sidewall extending from the base portion, and wherein the piezoelectric component is located on the base portion.

* * * * *